United States Patent
Koppes et al.

(10) Patent No.: US 6,919,453 B1
(45) Date of Patent: Jul. 19, 2005

(54) COLORANT COMPOSITIONS

(75) Inventors: William M. Koppes, Adelphi, MD (US); Michael E. Sitzmann, Adelphi, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 115 days.

(21) Appl. No.: 10/439,804

(22) Filed: May 19, 2003

Related U.S. Application Data

(63) Continuation-in-part of application No. 10/171,114, filed on Jun. 14, 2002, now Pat. No. 6,632,305, which is a continuation-in-part of application No. 09/874,946, filed on Jun. 6, 2001, now Pat. No. 6,423,844.

(51) Int. Cl.[7] ................ C07D 487/14; C06B 45/10; C06C 15/00; A61K 31/53
(52) U.S. Cl. ............. 544/198; 544/209; 8/405; 149/56
(58) Field of Search ................ 544/198, 206, 544/209

(56) References Cited

U.S. PATENT DOCUMENTS

| | | | |
|---|---|---|---|
| 2,473,797 A | 6/1949 | Kaiser et al. ............. 260/249.5 |
| 2,475,440 A | 7/1949 | Walter ........................ 260/239 |
| 3,061,605 A | 10/1962 | D'Alelio .................. 260/239.7 |
| 3,725,067 A | 4/1973 | Bailey et al. ................. 96/56.5 |
| 3,758,309 A | 9/1973 | Bailey et al. ................. 96/136 |
| 3,939,084 A | 2/1976 | Sullivan .................... 252/47.5 |
| 4,236,003 A | 11/1980 | Fletcher ..................... 544/254 |
| 4,549,018 A | 10/1985 | Siedle ........................ 544/225 |
| 4,565,815 A | 1/1986 | Kim et al. .................. 514/246 |
| 4,621,046 A | 11/1986 | Sato et al. .................. 430/381 |

FOREIGN PATENT DOCUMENTS

JP 49027287 A2 * 3/1974

OTHER PUBLICATIONS

Article: "The Synthesis and Dimeoth–Type Rearrangement of 5,7–Bis(dimethylamino)–3–(methylthio)–s–triazolo[4,3–a]–s–triazine", DeMilo et al., J. Heterocyclic Chem. 10, 231 (Apr. 1973), pp 231–233.

Article: "New Synthesis of Dyes of the Triazine", Series II. VAT Dyes of the Triazolo–Triazine Series by A. Titkov and I.D. Pletnev, Scientific Research Institute of Intermediates and Dyes, translated from Zhurnal Obshchel Khimil, vol. 33, No. 4, pp. 1355–1357, Apr. 1963.

Abstract: No. 93042a Basic azo dye. Maeda, Hhigeo et al. (40–Dyes, vol. 81, 1974), referencing Maeda et al. Japan Kokai 74 24,226.

Abstract: No. 122766x Basic azo dye. Maeda, Hhigeo et al. (40–Dyes, vol. 81, 1974), referencing Maeda et al. Japan Kokai 74 27,287.

Article: "Chemistry of Dicyandiamide V Structures of Guanazo– and Pyro–Guanazoles, and Reaction of Dicyandiamide with 3–Amino–5–Substituted–1,2,4,4H–Triazoles", kaiser et al. J. Organic Chemistry, vol. 18, 1953, pp. 1610–1614.

* cited by examiner

Primary Examiner—Venkataraman Balasubramanian
(74) Attorney, Agent, or Firm—Frederic Zimmerman

(57) ABSTRACT

Colorant compositions, and intermediate chemical compositions of colorant compositions are made from 1,2,4-triazolo[4,3-a][1,3,5]triazine-3,5,7-substituted compounds.

14 Claims, No Drawings

COLORANT COMPOSITIONS

This application is a continuation-in-part (CIP) of U.S. patent application Ser. No. 10/171,114, entitled "1,2,4-Triazolo[4,3-a][1,3,5]Triazine-3,5,7-Substituted Precursor, and Process, and Compounds Therefrom", filed Jun. 14, 2002, now U.S. Pat. No. 6,632,305, which is a continuation-in-part (CIP) of U.S. patent application Ser. No. 09/874,946, entitled "Process for Making 1,2,4-Triazolo[4,3-a][1,3,5]Triazine-3,5,7-Triamine", filed Jun. 6, 2001, now U.S. Pat. No. 6,423,844, issued Jul. 23, 2002.

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The present invention pertains to novel chemical fused ring structures useful in colorant compositions, such as dyes, pigments and other color applications.

2. Brief Description of the Related Art

Development of specialized chemical compounds requires proper precursor chemical structures. Current methods that purport to synthesize 1,2,4-triazolo[4,3-a][1,3,5]triazine-3,5,7-triamine all involve heating dicyandiamide and hydrazine dihydrochloride at elevated temperatures (100° C. or higher) for significant amounts of time in order to condense the dicyandiamide. This method was described by Kaiser et al. in a paper published in the Journal of Organic Chemistry, Vol. 18, 1953, page 1610.

Using this synthesis method theoretically provides for two possible isomeric structures of triazolotriazinetriamine (see I and II below). The first structure is the [4,3-a] triazolotriazinetriamine, pictured below as I. The second structure is the [1,5-a] triazolotriazinetriamine, pictured below as II. The product by Kaiser et al., resulting from the method above, was assigned the structure of I based upon degradation/oxidation studies of the product. However, these types of studies provide for a large degree of uncertainty as to structure.

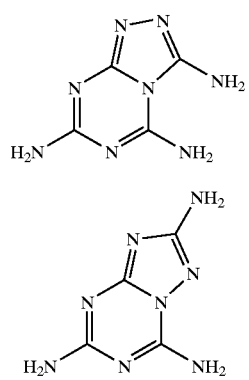

Recently, product derived from the above process was tested using X-ray diffraction, an extremely reliable technique, and, rather than the expected product I as originally reported, it was found that the actual structure of the product was that of II. The commercial product based upon the above method, sold under the names 3,5,7-triamino-s-triazolo[4,3-a]-s-triazine or 3,5,7-triamino-1,2,4-triazolo[4,3-a]-1,3,5-triazine, has also been tested via X-ray diffraction and found to be the structure of II. Because of the above error, prior to the present invention, there is, therefore, no known process of synthesizing product I. Additionally articles such as "New Synthesis of Dyes of the Triazine", Series II. VAT Dyes of the Triazolo-Triazine Series by A. Titkov and I. D. Pletnev, Scientific Research Institute of Intermediates and Dyes, translated from Zhurnal Obshchel Khimil, Vol. 33, No. 4, pp. 1355–1357, April 1963 (see also Maeda et al. Japan Kokai 74 24,226 and 74 27,287), are apparent mislabelings of the 3,5,7-Triamino-s-triazolo (1,5-a)-s-triazine.

The effects of the structural difference between these two products on the chemical and physical properties are of interest in any application of monotriazolotriazine ring systems. An analysis of densities and potential energy releases of the products reveals that the product I has a higher potential energy release value than product II that is significant in defense related energetic systems. The product II has also been investigated for use in the dye industry as a chromophore coupled to anthraquinones and indoles, and, therefore, product I should have similar potential uses. Other aromatic structure systems also are of interest.

Due to the discovery that the chemical sold as product I is actually product II, and the chemical and physical properties of the two products are significant for many uses, it would be desirable to derive product I, and like compounds, provide for synthesis of such compounds, as well as developing compounds from processes using product I and like compounds as a precursor.

SUMMARY OF THE INVENTION

The present invention includes a dye comprising a formula of:

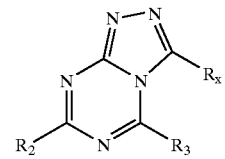

wherein $R_2$ and $R_3$ independently comprise electron donating groups, and Rx comprises an elongated conjugation sufficient to create a chromogen, with Rx preferably a chromophore, including azo dyes, having a (—N=N—) linkage or imino dyes having a (—N=$CR_aR_b$) linkage, such as (—N=$CR_aAr_x$), where at least one $R_a$ or $R_b$ represent an additional dye forming substituent, such as aryl groups, e.g., multiple and/or fused aryl groups ($Ar_x$).

Preferably the dye comprises the formula of:

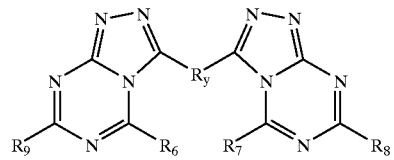

wherein $R_9$, $R_6$, $R_7$, and $R_8$ are electron donating groups, more preferably with $R_8$ and $R_9$ being —$NH_2$ and $R_6$ and $R_7$ being electron donating groups, and most preferably with $R_6$, $R_7$, $R_8$, and $R_9$ being —$NH_2$; and $R_y$ being —N=N—.

DETAILED DESCRIPTION OF THE INVENTION

The present invention includes a process for making a 1,2,4-triazolo[4,3-a][1,3,5]triazine-3,5,7-substituted compound, acid salt, particularly 1,2,4-triazolo[4,3-a][1,3,5]triazine-3,5,7-triamine, acid salt and a process for neutralizing the acid salt to make a 1,2,4-triazolo[4,3-a][1,3,5]triazine-3,5,7-substituted compound, particularly 1,2,4-triazolo[4,3-a][1,3,5]triazine-3,5,7-triamine, as well as the product of this process (the 1,2,4-triazolo[1,4,3-a][1,3,5]triazine-3,5,7-substituted compound, including the 1,2,4-triazolo[4,3-a][1,3,5]triazine-3,5,7-triamine is referred to herein as the "precursor"). Because of the reactive properties of the precursor, this precursor is useful in deriving compounds for ingredients in colorants and related compositions, as later described.

Colorants generally refer to dyes and pigments, as well as other applications that provide a contrasting coloration to a surface or composition. Dyes are generally applied to a substrate from a liquid. Pigments are generally attached to a substrate by additional adhering compounds. General concepts of color chemistry is disclosed in Colour Chemistry, by R. M. Christie, RSC Paperbacks, Heriot-Watt University Scottish Borders Campus, UK, Royal Society of Chemistry, 2001, the disclosure of which is hereby incorporated by reference.

The general process involves ring closure of a 2,4-substituted diamino-6-hydrazino-s-triazine with an acid and a chemical of the general formula RCN where the R comprises a leaving group, and then neutralizing said acid. Because the hydrazine nitrogen atoms that form the triazole ring are already in place on the 2,4-substituted-6-hydrazino-s-triazine, the final product formed is the desired [4,3-a] isomer, rather than the [1,5-a] isomer produced by the conventional dicyandiamide/hydrazine dihydrochloride methods. The general formulas for the process are set forth below:

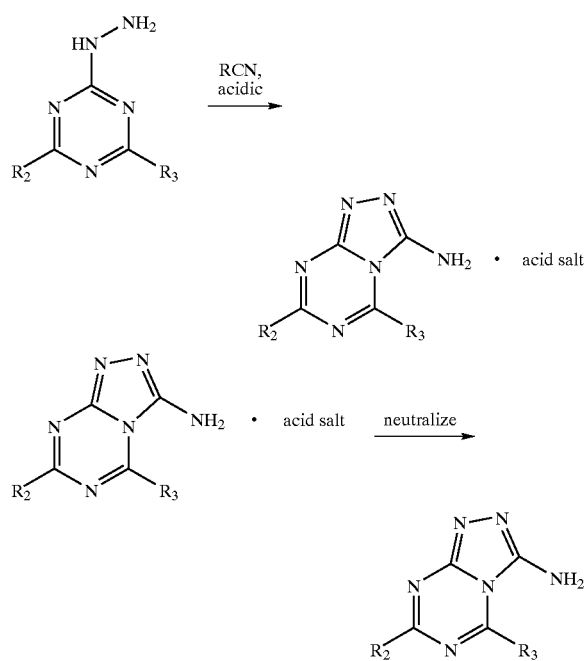

wherein the R comprises a leaving group, and $R_2$ and $R_3$ comprise electron donating groups.

More specifically, first, the invention comprises a process for the preparation of 1,2,4-triazolo[4,3-a][1,3,5]triazine-3,5,7-substituted compound, acid salt, with an amino group of the triazolo ring in practicing the present invention, one may first obtain or synthesize 2,4-diamino-6-hydrazino-s-triazine. One method for synthesizing this chemical is set forth in U.S. Pat. No. 3,061,605 by D'Alelio. The general method is to effect a reaction between 2,4-diamino-6-chloro-1,3,5-triazine and hydrazine. A specific example is set forth in column 3, lines 60–70 of the above patent and are hereby incorporated by reference. While this particular method of synthesizing 2,4-diamino-6-hydrazino-s-triazine is specifically disclosed, any prior art method of synthesis would be appropriate to practice the present invention.

The first step in the present invention comprises dissolving the 2,4-diamino-6-hydrazino-s-triazine with an acid. This step is preferably carried out at room temperature with an acid that is of sufficient strength to dissolve the 2,4-diamino-6-hydrazino-s-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid.

The second step comprises mixing the dissolved 2,4-diamino-6-hydrazino-s-triazine with a reagent of the formula RCN, wherein R comprises a leaving group. This reaction provides the amino triazole ring on the product directly. A leaving group, as used in this application, is a group that can be displaced to give ring closure; that is, produces the amino triazole ring. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. It is also preferred that the acid salt crystals be removed after the reaction is substantially complete, approximately thirty hours, to prohibit contamination of the final product with impurities. The crystals may be removed by any normal method, such as filtration, and can then be washed and dried in order to obtain the final acid salt product.

The present invention also comprises a process to take the 1,2,4-triazolo[4,3-a][1,3,5]triazine-3,5,7-triamine, acid salt synthesized above, and neutralize the acid salt crystals in order to obtain a final product of 1,2,4-triazolo[4,3-a][1,3,5]triazine-3,5,7-triamine. This process involves the steps described above as well as the following steps.

First, the acid salt crystals are removed from the solution synthesized above. Then, the acid salt crystals are neutralized by mixing them with a substance more basic than 1,2,4-triazolo[4,3-a][1,3,5]triazine-3,5,7-triamine. This step results in the removal of the acid from the above reaction and provides for a final product of 1,2,4-triazolo[4,3-a][1,3,5]triazine-3,5,7-triamine. The substance used in this final step may be selected by one skilled in the art based upon the basicity of the substance versus the basicity of 1,2,4-triazolo[4,3-a][1,3,5]triazine-3,5,7-triamine. Some examples are potassium carbonate, potassium acetate, sodium bicarbonate, and sodium hydroxide. One preferred substance is potassium carbonate. It is also preferred that the reaction take place in solution, so preferably, water or some other solvent may be added to the salt.

Due to the reactive nature of the —$NH_2$ from the five-member ring, derivatives of the precursor, particularly tricyclic fused compounds as described below, are useful in forming colorants such as dyes, pigments and other color applicants, such as without limitation paints, textile colorants and/or indicators, including liquid crystal uses and other indicators for computer display screens (see e.g., U.S. Pat. Nos. 3,758,309 and 3,725,067 to Bailey et al., U.S. Pat. No. 4,236,003 to Fletcher, and U.S. Pat. No. 4,621,046 to Sato et al.). Food and drug color applications, and photochemical applications, such as conductors and catalyst, may be developed herein.

As used herein, an "electron donating group" designates a group that will release or donate electrons more than hydrogen would if it occupied the same position in the molecule. See J. March, Advanced Organic Chemistry, $3^{rd}$ Ed., John Wiley & Sons p. 238 (1985). These types of groups are well known in the art. Examples include lower alkylamino, di-loweralkylamino, amino, halo, aryl, lower alkoxy, lower aralkoxy, aryloxy, mercapto, lower alkylthio, and the like, including for example, $O^-$, $—COO^-$, $—OR_\alpha$, $—CR_\alpha R_\beta R_\gamma$, $—OCOR_\alpha$, $—NR_\alpha N_\beta$, and $SR_\alpha$, where $R_\alpha$, $R_\beta$, and $R_\gamma$ groups are independently H or an alkyl group, such as methyl, ethyl, propyl, isopropyl, tert-butyl, isobutyl, and the like. The preferred electron donating groups are amino, hydroxy, lower alkoxy, lower alkylamino and di-loweralkylamino. The most preferred electron donating group is amino. Lower used herein denotes straight-chain and branched hydrocarbon moieties containing from about 1 to about 8 carbon atoms. Electron donating groups include atoms that can stabilize the developing positive charge in a ring closure by mesomeric effect, such as methoxy groups.

The present invention further includes a chromogen for providing a colorant of a dye or pigment comprising a formula of (referred to herein as "Formula A"):

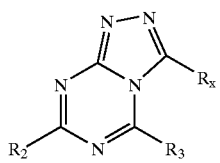

Formula A wherein $R_2$ and $R_3$ independently comprise electron donating groups, and Rx comprises an elongated conjugation sufficient to create a chromogen, with Rx preferably a chromophore, including azo dyes, having a ($—N=N—$) linkage or imino dyes having a ($—N=CR_aR_b$) linkage, such as ($—N=CR_aAr_x$), where at least one $R_a$ and $R_b$ represent an additional dye forming substituent, such as aryl groups, e.g., multiple and/or fused aryl groups ($Ar_x$). Representative units within the Rx group include anthraquinones, triphenylmethanes, azines, phthalocyanines, indoles, and the like.

Rx may include groups that create polyene dyes ($—CH=$), including polymethine ($—CR=$) and aza analogues ($—N=$) dyes, such as diarylmethine dyes and triarylmethine dyes, and azomethine ($N=CH—$), with the appropriate replacing group of the Rx determinable by those skilled in the art.

Anthraquinones derivatives of the precursor, such as haloanthraquinones, including chloroanthraquinones, bromoanthraquinones, fluoroanthraquinones, etc., nitroanthraquinones, sulfonated anthraquinones, alkylanthraquinones, anthraquinonecarboxylic acids and aldehydes, aminoanthraquinones, hydroxyanthraquinones, anthraquinone ethers, anthraquinonethiols, and the like, their combinations, either incorporated within a final colorant, or as an intermediate of the final colorant, may be used.

Derivatives of triphenylmethanes, diphenylmethanes, xanthene, acridine, oxazine, azine, and the like, their combinations, either incorporated within a final colorant, or as an intermediate of the final colorant, may be used.

Other known colorants may be incorporated within a final colorant, or as an intermediate of the final colorant, such as phthalocyanines, phthanloylacridones, carbonyl nitro, nitroso or indole derivatives, imines with reactive carbonyl units, such as ketone or aldehyde, diazonium and imine compounds, aromatic compounds susceptible to electrophillic attack, and amines with reactive carbonyl, such as ketones or aldehyde compounds.

Azo dyes may be formed from the [4,3-a] isomer by oxidation coupling reaction, described in Examples 2A and 2B. Oxidative coupling reactions to form azo dyes do not occur with the [1,5-a] isomer, and reaction of the [1,5-a] isomer with aqueous sodium bicarbonate/iodine gives no reaction. The oxidative coupling of the [4,3-a] isomer is not limited to iodine as oxidizing agent. Other halogens including chlorine and bromine can be used, as well as other appropriate non-halogen oxidizing agents. In addition, the oxidative coupling reaction could be performed in the presence of other amines ($RNH_2$) to produce other new azo dyes. The coupling reaction exemplified in Examples 2A and 2B are dye forming reactions and particularly useful in creating compounds having a single triazolodiaminotriazine unit, i.e., two joined units of Formula A. Alternatively a second anime may be combined with a triazolodiaminotriazine unit, i.e., Formula A, by incorporating the second amine into the reaction. Preferably the second amine has similar solubility as the triazolodiaminotriazine unit, and more preferably equivalent amounts of the second amine and the triazolodiaminotriazine unit are reacted. The second amine may include for example, without limitation, aromatic, primary amines with, such as those of similar reactivity to the triazolodiaminotriazine unit, including para-nitroaniline.

In addition to the oxidative coupling reaction exemplified in Example 2A and 2B, dyes may be formed by diazotization of the amino group on the triazole ring of an aminotriazolotriazine to produce a diazonium salt and then coupling the diazonium salt (diazo coupling) with various aromatic compounds, as exemplified in Example 3 and prophetic Example 4. Preparation of the aminotriazolotriazine may be accomplished by using an electron donating group on the $R_2$ and $R_3$ positions to promote the cyclization of the 2,4-disubstituted hydrazinotriazine with cyanogen bromide. It is noted that Dimroth Rearrangementa of triazolotriazines may occur, as disclosed in "The Synthesis and Dimroth-Type Rearrangement of 5,7-Bis(dimethylamino)-3-(methylthio)-s-triazolo[4,3-a]-s-triazine", DeMilo et al., J. Heterocyclic Chem. 10, 231 (April 1973), pp 231–233, the disclosure of which is herein incorporated by reference, in certain instances, with determination of the proper reaction conditions to avoid this Dimroth Rearrangement determinable by those skilled in the art of colorants in light of the disclosure herein. The aminotriazolotriazine is converted to the diazonium salt, which is then available to react with various aromatic compounds to form azo dyes, such as those similar to the patent referenced herein. Appropriate electron-donating groups allow formation of the appropriate aminotriazolotriazine but will not undergo reaction with the diazonium salt intermediate. Such electron donating groups include such substituents as $—OR$, $—NR_1R_2$, $—SR$, etc, with R comprising lower straight-chain and branched hydrocarbon moieties having from about 1 to about 8 carbon atoms. An example of a blocking group would be the methoxy group. With the incorporation of an electron donating/blocking group, the diazonium salt cannot udergo internal cyclization and is available for reaction with various aromatic compounds, thereby creating the $—N=N—$ unit of the azo dye.

In one preferred embodiment, the dye comprises the formula:

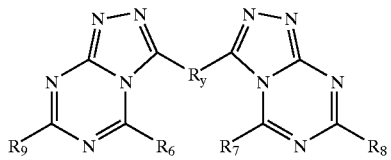

wherein $R_9$, $R_6$, $R_7$, and $R_8$ are electron donating groups, more preferably with $R_8$ and $R_9$ being —$NH_2$, and most preferably with $R_9$, $R_6$, $R_7$, and $R_8$ are —$NH_2$; and $R_y$ is —N=N—.

In another preferred embodiment, the dye comprises the formula:

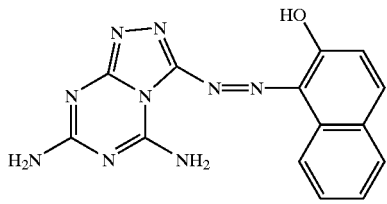

Precursor

The precursor comprises a 1,2,4-triazolo[4,3-a][1,3,5]triazine-3,5,7-substituted compound, acid salt or its neutralized form of the 1,2,4-triazolo[4,3-a][1,3,5]triazine-3,5,7-substituted compound, preferably 1,2,4-triazolo[4,3-a][1,3,5]triazine-3,5,7-triamine. The general process involves ring closure of 2,4-diamino-6-hydrazino-s-triazine with an acid and a chemical of the general formula RCN where the R comprises a leaving group, and then neutralizing the acid. An example of the reaction using the 1,2,4-triazolo[4,3-a][3,5]triazine-3,5,7-triamine is shown below (with R=Br and acid=HCl).

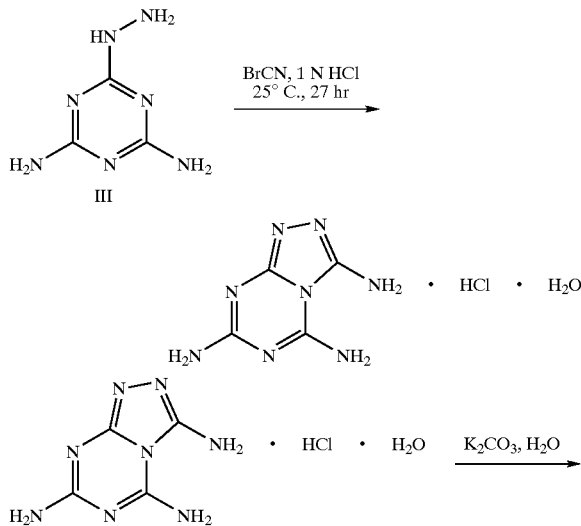

-continued

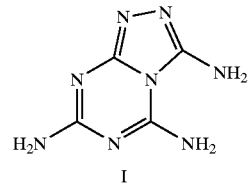

The structure of the precursor, with $R_1$, $R_2$ and $R_3$ all $NH_2$, is shown below:

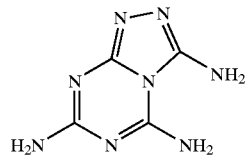

More specifically the preferred embodiment, the 1,2,4-triazolo[4,3-a][1,3,5]triazine-3,5,7-triamine, acid salt is derived first by obtaining or synthesizing 2,4-diamino-6-hydrazino-s-triazine. One method for synthesizing this chemical is set forth in U.S. Pat. No. 3,061,605 by D'Alelio. The general method is to effect a reaction between 2,4-diamino-6-chloro-1,3,5-triazine and hydrazine. A specific example is set forth in column 3, lines 60–70 of the above patent which is hereby incorporated by reference. While this particular method of synthesizing 2,4-diamino-6-hydrazino-s-triazine is specifically disclosed, any method of synthesis would be appropriate to practice the present invention. The 2,4-diamino-6-hydrazino-s-triazine is dissolved with an acid, preferably out at room temperature with an acid that is of sufficient strength to dissolve the 2,4-diamino-6-hydrazino-s-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid. The dissolved 2,4-diamino-6-hydrazino-s-triazine is mixed with a reagent of the formula RCN, wherein R comprises a leaving group. This reaction will provide the amino triazole ring on the product directly. A leaving group, as used in this application, is a group that can be displaced to give ring closure; that is, produces the amino triazole ring. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. It is also preferred that the acid salt crystals be removed after the reaction is substantially complete, approximately thirty hours, to prohibit contamination of the final product with impurities. The crystals may be removed by any normal method, such as filtration, and can then be washed and dried in order to obtain the final acid salt product.

Neutralization of the 1,2,4-triazolo[4,3-a][1,3,5]triazine-3,5,7-triamine, acid salt crystals synthesized above to obtain a final product of 1,2,4-triazolo[4,3-a][1,3,5]triazine-3,5,7-triamine is accomplished by mixing the crystals with a substance more basic than 1,2,4-triazolo[4,3-a][1,3,5]triazine-3,5,7-triamine. This step results in the removal of the acid from the above reaction and provides for a final product of 1,2,4-triazolo[4,3-a][1,3,5]triazine-3,5,7-triamine. The substance used in this final step may be selected by one skilled in the art based upon the basicity of the substance versus the basicity of 1,2,4-triazolo[4,3-a][1,3,5]triazine-3,5,7-triamine. Some examples are potassium carbonate, potassium acetate, sodium bicarbonate, and sodium hydroxide. One preferred substance is potassium carbonate. It is also preferred that the reaction take place in solution, so preferably, water or some other solvent may be added to the salt.

The following examples (Examples 1A–1C) are preparations of the 1,2,4-triazolo[4,3-a][1,3,5]triazine-3,5,7-triamine precursors, with the chemical structures shown below:

EXAMPLE 1A

Preparation of 1,2,4-triazolo[4,3-a][1,3,5]triazine-3,5,7-triamine, Hydrochloric Salt Hydrate To 126 g of 1 N hydrochloric acid stirred at 25° C. was added 9.06 g (0.0570 mole) of 2,4-diamino-6-hydrazino-s-triazine [prepared according to G. F. D'alelio, U.S. Pat. No. 3,061,605 (1962), which is incorporated herein by reference]. The mixture was stirred for 10 minutes, at which time nearly all of the 2,4-diamino-6-hydrazino-s-triazine had dissolved. Cyanogen bromide (9.3 g, 0.0877 mole) was added at one time and, after 5 minutes, all of the material was in solution. After about 1 hour, crystals began to precipitate. After 3 hours, stirring was stopped and the mixture was allowed to stand for an additional 24 hours to continue precipitation of crystals. The crystals were removed by filtration and washed with 2×25 ml cold water. The crystals were air dried and then dried in a vacuum desiccator over Drierite to give 8.60 g (68.4% yield) of product. IR (KBr): 3300, 3155, 1708, 1695, 1624, 1534, 1490, 1444, 1339, 1173, 1073, 979, 845, 772 cm$^{-1}$. Anal. Calcd for $C_4H_6N_8$ (HCl) ($H_2O$): C, 21.77; H, 4.11; N, 50.79; Cl, 16.07. Found: C, 21.84; H, 4.25; N, 50.02; Cl, 16.02.

EXAMPLE 1B

Preparation of 1,2,4-triazolo[4,3-a][1,3,5]triazine-3,5,7-triamine

To 6.86 g (0.031 mole) of 1,2,4-triazolo[4,3-a][1,3,5]triazine-3,5,7-triamine, hydrochloric salt hydrate stirred in 175 ml of water was added 4.40 g (0.031 mole) of potassium carbonate and the mixture was stirred vigorously for 40 minutes. The solid was removed by filtration, washed with water, and dried to give 4.83 g (94%) of 1,2,4-triazolo[4,3-a][1,3,5]triazine-3,5,7-triamine. $^{13}$C NMR ($CD_3CO_2D/D_2O$, 1:1 by vol): 145.7, 151.1, 151.9, 164.0. $^{13}$C NMR ($D_2SO_4$): 133.6, 141.9, 143.1, 149.5. IR (KBr): 3413, 3314, 3096, 1654, 1611, 1540, 1480, 1430, 1375, 979, 859, 770 cm$^{-1}$. Anal. Calcd for $C_4H_6N_8$: C, 28.92; H, 3.64; N, 67.44. Found: C, 28.64; H, 3.65; N, 66.08.

EXAMPLE 1C

Preparation of 1,2,4-triazolo[4,3-a][1,3,5]triazine-3,5,7-triamine, Hydrochloric Salt Hydrate To 0.31 g (0.003 mole) of 37% hydrochloric acid in water (4 ml) and methanol (21 ml) stirred at 25° C. was added 0.42 g (0.003 mole) of 2,4-diamino-6-hydrazino-s-triazine [prepared according to G. F. D'alelio, U.S. Pat. No. 3,061,605 (1962)]. Cyanogen bromide (0.32 g, 0.003 mole) was then added at one time. The solution was held at 77–80° C. for 3 hours, before it was cooled to 25° C. and a small amount of solid was removed by filtration. The volatiles were removed from the filtrate to give 0.60 g of solid that was mainly 1,2,4-triazolo[4,3-a][1,3,5]triazine-3,5,7-triamine, hydrochloric salt hydrate by TLC and IR analyses.

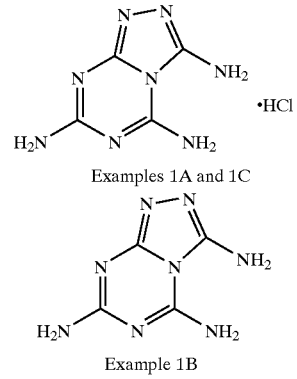

Examples 1A and 1C

Example 1B

Preparation of colorants are exemplified below.

EXAMPLE 2A

Preparation of azo(triazolodiaminotriazine)

A mixture of 0.30 g (1.8 mmol) of finely ground 1,2,4-triazolo[4,3-a][1,3,5]triazine-3,5,7-triamine in 35 ml of water was stirred vigorously at 25° C. during the addition of 0.60 g (7.2 mmol) of sodium bicarbonate and 0.90 g (3.6 mmol) of iodine. The mixture rapidly turned deep purple in color. Stirring was continued for 90 hours before the insoluble dark purple solid was removed by filtration, washed with water and dried to give (0.22 g, 71%). $^1$H NMR ($D_2SO_4$): 10.2 (s); $^{13}$C NMR ($D_2SO_4$): 139.2, 141.7, 142,6, 146.2.

EXAMPLE 2B

Preparation of azo(triazolodiaminotriazine)

A beaker containing a solution of 120 mg (0.72 mmol) of 1,2,4-triazolo[4,3-a][1,3,5]triazine-3,5,7-triamine and 360 mg (4.3 mmol) of sodium bicarbonate in 1 liter of water was placed in a closed container with iodine crystals (1.4 g). After 48 hours, sufficient iodine had sublimed and was absorbed by the water to produce 70 mg (56%) of dark purple solid precipitate. Anal. Calcd for $C_8H_8N_{16}$ ($H_2O$): C, 27.75; H, 2.91; N, 64.72. Found: C, 27.47; H, 3.00; N, 62.65.

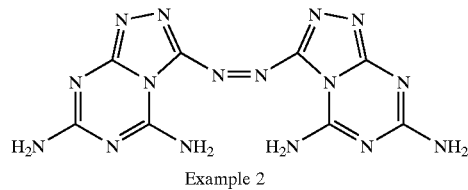

Example 2

EXAMPLE 3

Preparation of azo(triazolodlaminotriazine)(2-naphthol)

Preparation of diazonium salt: Aminotriazolo-diaminotriazine, hydrochloride salt was prepared from 2,4-diamino-6-hydrazinotriazine and cyanogen bromide as described in Example 1A. The diazonium salt was produced by stirring the aminotriazolo-diaminotriazine, hydrochloride salt in aqueous sodium nitrite. For example, sodium nitrite (1.5 g, 21.7 mmole) was added in one portion to the aminotriazolo-diaminotriazine, hydrochloride salt hydrate (0.50 g, 2.27 mmole) stirred in 15 ml of water at 23° C. The mixture was stirred at 22–23° C. for 4 hours and then was filtered to give an orange insoluble solid that was washed with cold water. The orange solid (diazonium salt) (see general structure below with $R_2$ and $R_3$ being $NH_2$) was air-dried to a weight of 0.38 g.

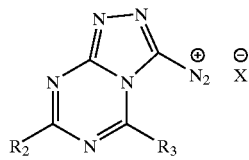

Diazonium Salt (General Structure)

For the diazonium salt, X is a counterion to balance the salt, such as Cl, $NO_2$, $HSO_4$, $BF_4$, etc., with the counterion being determinable by those skilled in the art.
Preparation of azo(triazolodiaminotriazine)(2-naphthol): A 0.10 g sample of the orange solid (diazonium salt) was stirred in 15 ml of acetic acid-water (70/30 v/v) at 25° C. Addition of 2-naphthol (0.20 g) to the stirred yellow mixture produced a deep red solution and eventually a dark red precipitate. After 2 hours, the precipitate was removed by filtration and washed with methanol to give 0.11 g of dark red (burgundy) colored solid azo dye. A second crop (0.04 g) of azo dye was obtained by removal of solvent from the filtrate under reduced pressure and then adding methanol. $^1$H NMR (DMSO-$d_6$) of the azo dye: 4.15 (very broad, OH+$H_2O$); 6.90 (broad s, $NH_2$); 7.31–7.78; 8.56, multiplets, naphthyl-H); 9.15 (broad s, $NH_2$). $^{13}$C NMR (DMSO-$d_6$) of the azo dye: 122.0, 124.3, 127.4, 128.0, 128.1, 133.4 (very broad), 136.3 (broad), 139.4, 150.8, 151.9, 163.0, 166.6.

The azo dye dissolves in DMSO to give a very deep red burgundy colored solution. High dilution of a drop of the DMSO solution with solvents such as methanol, water or reagent grade acetone produced reddish solutions. High dilution with technical grade acetone produced a deep bluish purple solution. The structure of Example 3 follows:

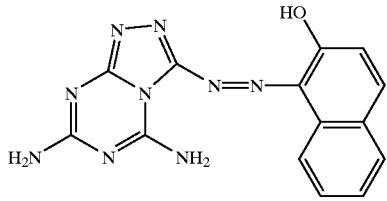

Example 3

EXAMPLE 4 (PROPHETIC)

EXAMPLE 4A

Preparation of azo(triazolodiaminotriazine)(p-dimethylaminobenzene)

An aminotriazolo-substituted triazine salt, such as aminotriazolo-diaminotriazine, hydrochloride salt is prepared from 2,4-diamino-6-hydrazinotriazine and cyanogen bromide as described in Example 1A. The diazonium salt (see general structure with $R_2$ and $R_3$ being $NH_2$) is produced from the aminotriazolo-diaminotriazine, hydrochloride salt as in Example 3. The diazaonium salt is combined with N,N-dimethylaniline in solvent (similar to Example 3) to give the azo coupled product (4A).

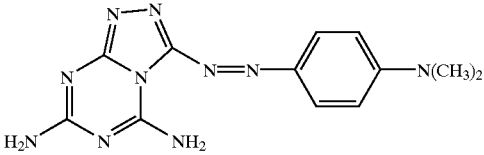

Example 4A

EXAMPLE 4B

Preparation of azo(triazolodiaminotriazine)(N-aryl-methylpyrazolone)

Aminotriazolo-diaminotriazine, hydrochloride salt is prepared from 2,4-diamino-6-hydrazinotriazine and cyanogen bromide as described in Example 1A. The diazonium salt (see general structure; $R_2$ and $R_3$ being $NH_2$) is produced as in Example 3 and the diazonium salt is combined with N-aryl-methylpyrazolone in solvent (similar to Example 3) to give the azo coupled product (4B).

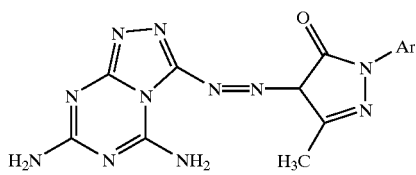

Example 4B

EXAMPLE 4C

Preparation of azo(triazolodiaminotriazine) (aminonaphthol-disulfonic acid)

Aminotriazolo-diaminotriazine, hydrochloride salt is prepared from 2,4-diamino-6-hydrazinotriazine and cyanogen bromide as described in Example 1A. The diazonium salt (see general structure; $R_2$ and $R_3$ being $NH_2$) is produced as in Example 3 and the diazonium salt is combined with aminonaphthol-disulfonic acid solution under weakly acidic conditions to give the azo coupled product (4C).

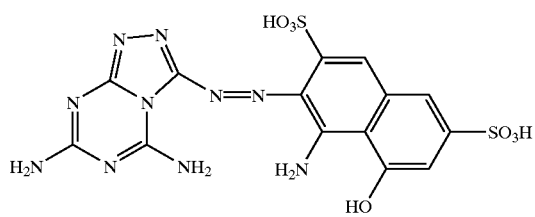

Example 4C

EXAMPLE 4D

Preparation of azo(triazolodimethoxytriazine) (phenol)

Aminotriazolo-dimethoxytriazine, hydrochloride salt is prepared from 2,4-dimethoxy-6-hydrazinotriazine and cyanogen bromide in a similar manner to the method described in Example 1A. Diazotization of the aminotriazolo-dimethoxytriazine, hydrochloride salt is performed by: (a) adding portion-wise a slurry of the aminotriazolo-diaminotriazine, hydrochloride salt in dilute hydrochloric acid to stirred ice cold aqueous sodium nitrite or (b) slowly adding dilute hydrochloric acid to stirred ice cold aqueous sodium nitrite containing the aminotriazolo-diaminotriazine, hydrochloric salt. Colder reaction temperatures may be necessary is some cases in the preparation of the diazonium salt to ensure it does not undergo reaction/decomposition before it is added to an aromatic compound due to the absence of $NH_2$ substituents. If necessary, at the end of the diazotization procedure, excess nitrous acid is destroyed by the addition of sulfamic acid. The diazonium salt (see general structure; $R_2$ and $R_3$ being $OCH_3$) is added to a phenol solution to give the azo coupled product (4D).

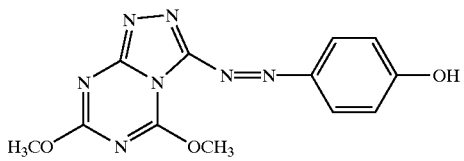

Example 4D

EXAMPLE 4E

Preparation of azo(triazolo-bis[dimethylamino]triazine)(2-naphthol)

Aminotriazolo-bis[dimethylamino]triazine, hydrochloride salt is prepared from 2,4-dimethylamino-6-hydrazinotriazine and cyanogen bromide in a similar manner to the method described in Example 1A. The diazonium salt (see general structure; $R_2$ and $R_3$ being $N(CH_3)_2$) is produced similar to Example 4D and then is added to cold 2-naphthol solution to give the azo coupled product (4E).

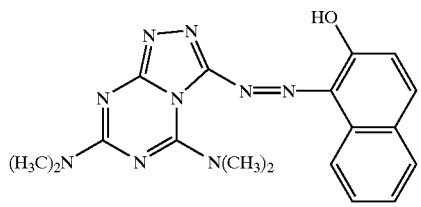

Example 4E

EXAMPLE 4F

Preparation of azo(triazoloaminomethoxytriazine)(p-dimethylamino-benzene)

Aminotriazoloaminomethoxytriazine, hydrochloride salt is prepared from 2-amino-4-methoxy-6-hydrazinotriazine and cyanogen bromide in a similar manner to the method described in Example 1A. Similar to Example 4D, the diazonium salt (see general structure; $R_2$ being $NH_2$ and $R_3$ being $OCH_3$) is produced and then is added to cold N,N-dimethylaniline solution to give the azo coupled product (4F). In this case, isomers are possible with either the amino- or the methoxy-substituent on the triazine ring being adjacent to the triazole amine. Example 4F is the product when the methoxy group is adjacent to the triazole amine.

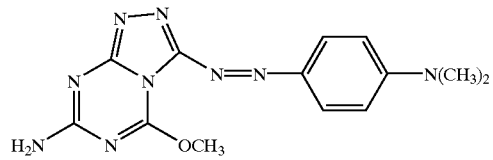

Example 4F

What is claimed is:

1. A compound having the chemical formula:

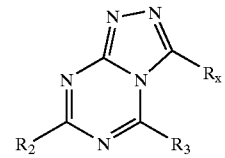

wherein $R_2$ and $R_3$ independently are electron donating groups, and Rx is a chromophore selected from the group of azo dyes having a —N=N— linkage to the triazole ring and imino dyes having a —N=$CR_aR_b$ linkage to the triazole ring wherein at least one $R_a$ or $R_b$ are dye forming substituents.

2. The compound of claim 1, wherein Rx is an azo dye having a —N=N— linkage.

3. The compound of claim 1, wherein Rx is —N=$CR_aR_b$, wherein at least $R_a$ or $R_b$ represents a dye forming substituent.

4. The compound of claim 3, wherein Rx is selected from the group consisting of anthraquinones, triphenylmethanes, azines, phthalocyanines, carbonyl, and indoles.

5. The compound of claim 1, wherein $R_2$ and $R_3$ independently are electron donating groups selected from the group consisting of lower alkylamino, di-loweralkylamino, amino, halo, aryl, lower alkoxy, lower aralkoxy, aryloxy, mercapto, hydroxy and lower alkylthio.

6. The compound of claim 1, wherein $R_2$ and $R_3$ independently are electron donating groups selected from the group consisting of a hydroxyl salt, a carboxyl salt, —$OR_\alpha$, —$CR_\alpha R_\beta R_\gamma$, —$OCOR_\alpha$, —$NR_\alpha R_\beta$, and $SR_\alpha$, where $R_\alpha$, $R_\beta$, and $R_\gamma$ groups are independently an alkyl group or H.

7. The compound of claim 1, wherein either $R_2$ and $R_3$ independently are —$NH_2$.

8. The compound of claim 1, wherein both $R_2$ and $R_3$ are —$NH_2$.

9. The compound of claim 1, wherein either $R_2$ and $R_3$ independently are —$OCH_3$.

10. The compound of claim 1, wherein both $R_2$ and $R_3$ are —$OCH_3$.

11. An intermediate chemical compound comprising a diazonium salt structure of:

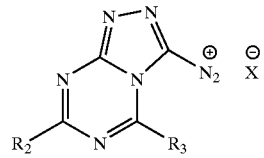

wherein $R_2$ and $R_3$, independently, are electron donating groups, and X is a counterion.

12. The intermediate chemical compound of claim 11, wherein $R_2$ and $R_3$ are both $NH_2$.

13. A colorant having the chemical structure of:
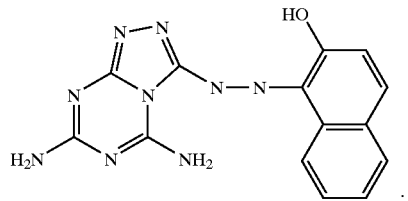
14. A colorant having the chemical structure of:
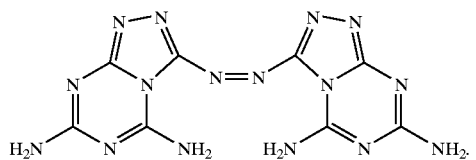
* * * * *